United States Patent [19]
Avoy

[11] Patent Number: 5,656,035
[45] Date of Patent: Aug. 12, 1997

[54] REFILLABLE FIBRINOGEN DISPENSING KIT

[76] Inventor: Donald R. Avoy, 5988 Garces Ave., San Jose, Calif. 95123

[21] Appl. No.: 428,670

[22] Filed: Apr. 25, 1995

[51] Int. Cl.$^6$ ................................................ A61M 5/00
[52] U.S. Cl. .................. 604/191; 604/88; 604/201; 141/2; 141/18; 222/82; 222/137; 222/255; 239/304; 239/306
[58] Field of Search .................... 604/232, 234, 604/235, 88, 148, 191, 200, 201, 181, 411–414; 222/82, 135, 137, 255, 630, 631; 239/304, 307, 309, 333, 303, 306; 141/2, 18, 20.5, 21, 22, 29

[56] References Cited

U.S. PATENT DOCUMENTS

| | | |
|---|---|---|
| 2,941,696 | 6/1960 | Homm . |
| 3,045,925 | 7/1962 | Giangualano . |
| 3,236,418 | 2/1966 | Dalle et al. . |
| 3,236,457 | 2/1966 | Kennedy et al. . |
| 3,269,389 | 8/1966 | Meurer et al. . |
| 3,405,706 | 10/1968 | Cinqualbre . |
| 3,604,410 | 9/1971 | Whitacre . |
| 3,714,943 | 2/1973 | Yanof et al. . |
| 3,760,986 | 9/1973 | Castner et al. . |
| 3,767,085 | 10/1973 | Cannon et al. . |
| 3,828,980 | 8/1974 | Creighton et al. . |
| 4,040,420 | 8/1977 | Speer . |
| 4,260,077 | 4/1981 | Schroeder . |
| 4,359,049 | 11/1982 | Redl et al. . |
| 4,581,015 | 4/1986 | Alfano ................................ 604/88 |
| 4,673,395 | 6/1987 | Phillips . |
| 4,674,658 | 6/1987 | Van Brocklin . |
| 4,697,622 | 10/1987 | Swift et al. . |
| 4,782,982 | 11/1988 | Ellison ................................ 141/2 |
| 4,826,048 | 5/1989 | Skorka et al. . |
| 4,902,281 | 2/1990 | Avoy . |
| 4,930,686 | 6/1990 | Ellison ................................ 141/2 |
| 5,049,135 | 9/1991 | Davis ................................ 604/191 |

FOREIGN PATENT DOCUMENTS 1232370  4/1960  France .

OTHER PUBLICATIONS

Parke-Davis Thrombin, USP Thrombostat Fact Sheet (Apr. 1986).
Calmar, Inc. TS-800 Fact Sheet.

*Primary Examiner*—John D. Yasko
*Assistant Examiner*—Ronald K. Stright, Jr.
*Attorney, Agent, or Firm*—Knobbe, Martens, Olson & Bear, LLP

[57] ABSTRACT

Disclosed is a refillable dispenser for separately dispensing each of two biological fluids contained therein for intermixing at a site outside of the dispenser to produce hemostasis or a tissue adhesive. The dispenser is compact, contains integrally formed internal reservoirs for the two biological fluids, an injection port on each reservoir for refilling the reservoir, and is designed for efficient filling without compromising the integrity of the sterile field. The dispenser is capable of dispensing the biological fluids, such as fibrinogen and thrombin, at either a focused point or in an aerosol mist. In addition, spray elements are disclosed for uniformly distributing the two biological fluids along either the interior surface or the exterior surface of an implantable vascular graft.

7 Claims, 5 Drawing Sheets

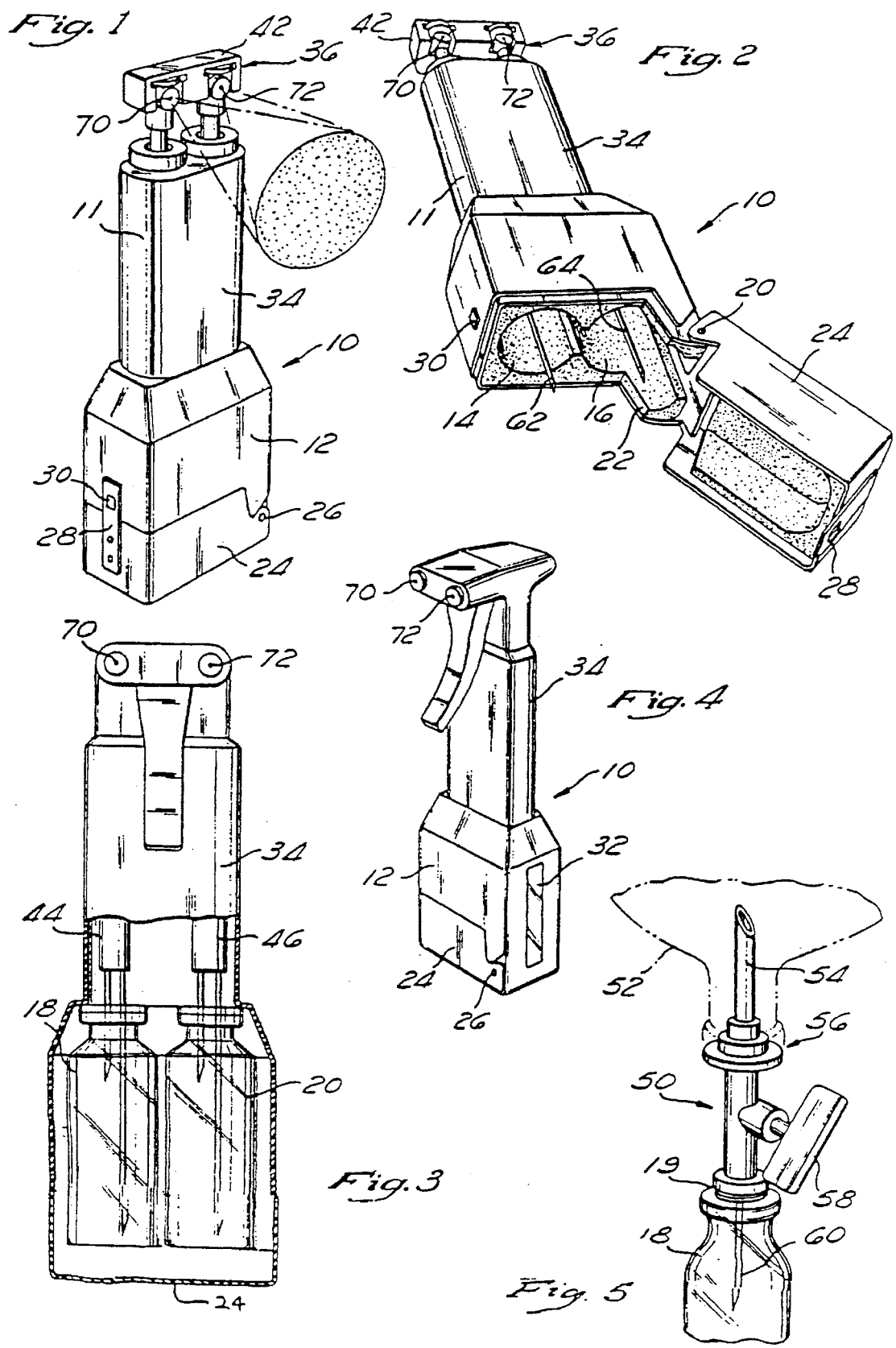

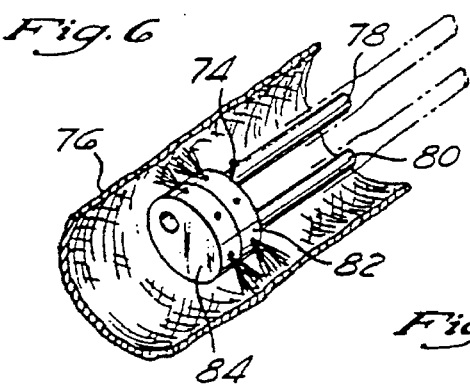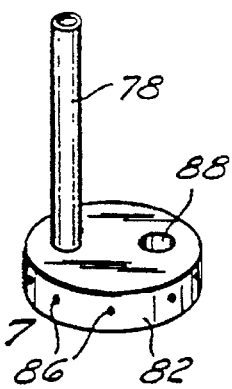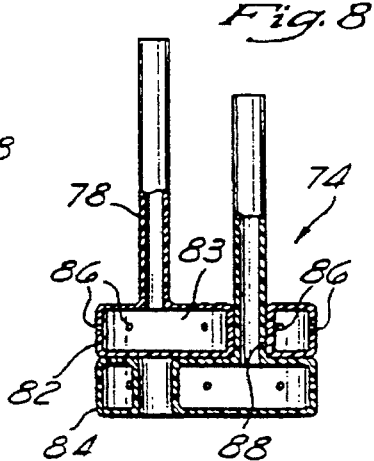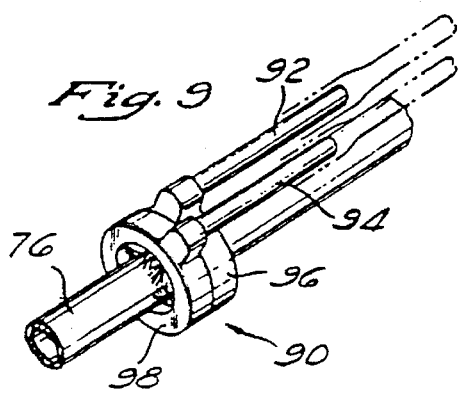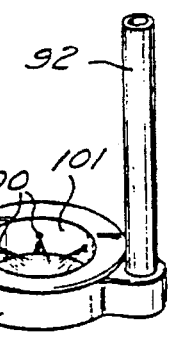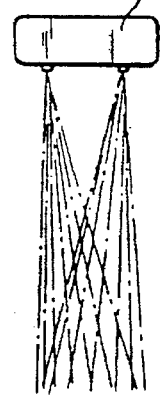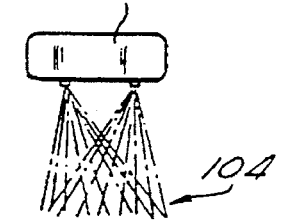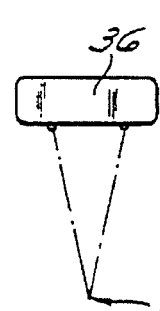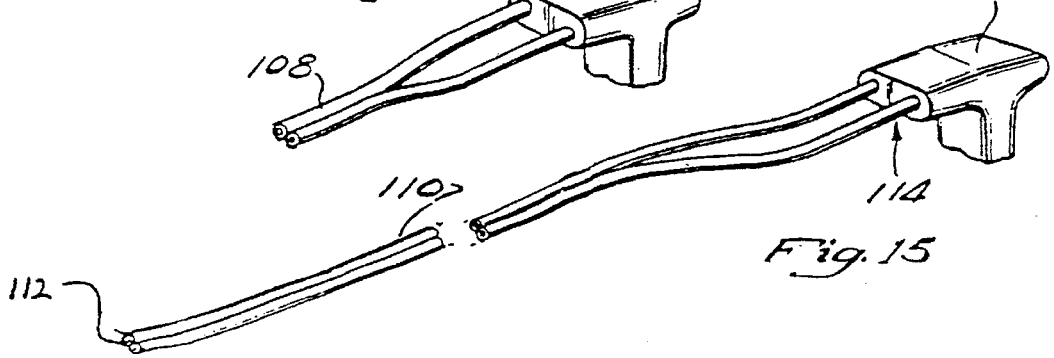

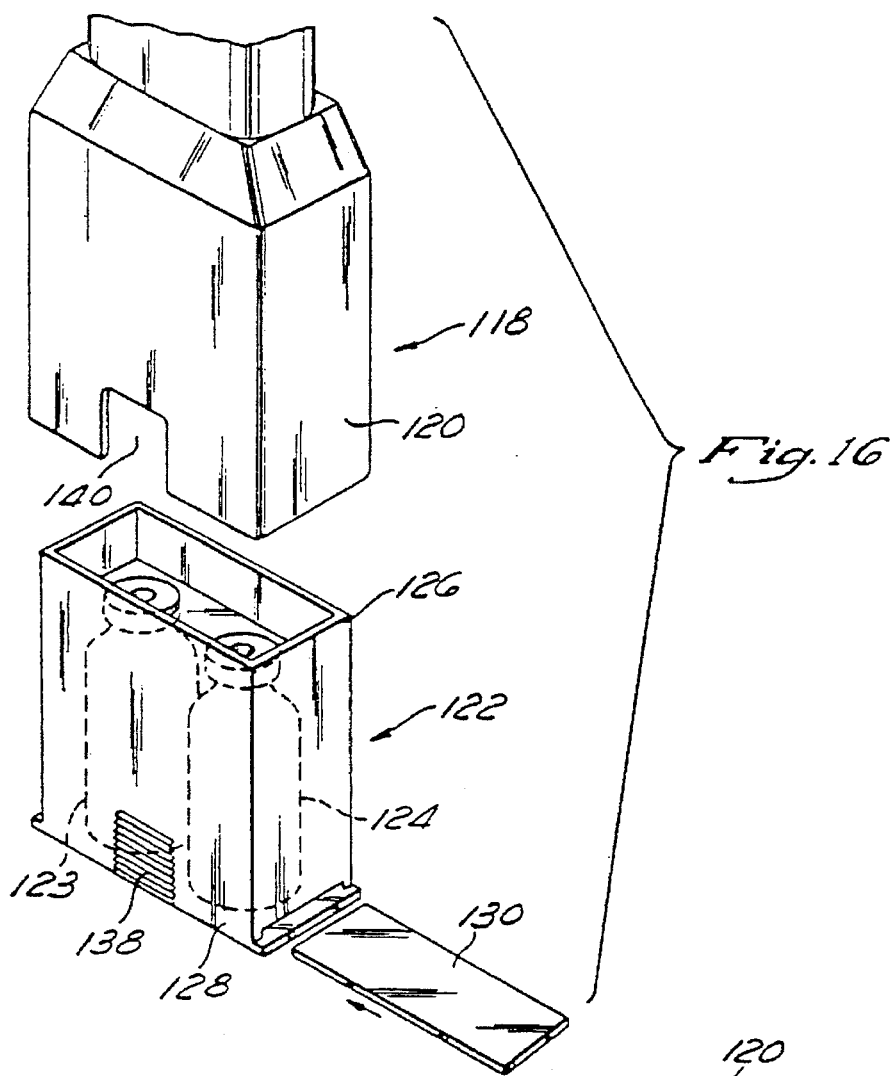
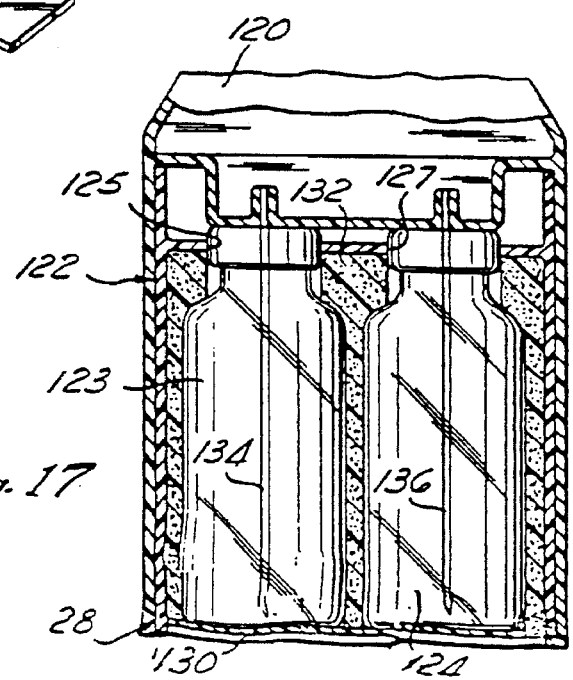

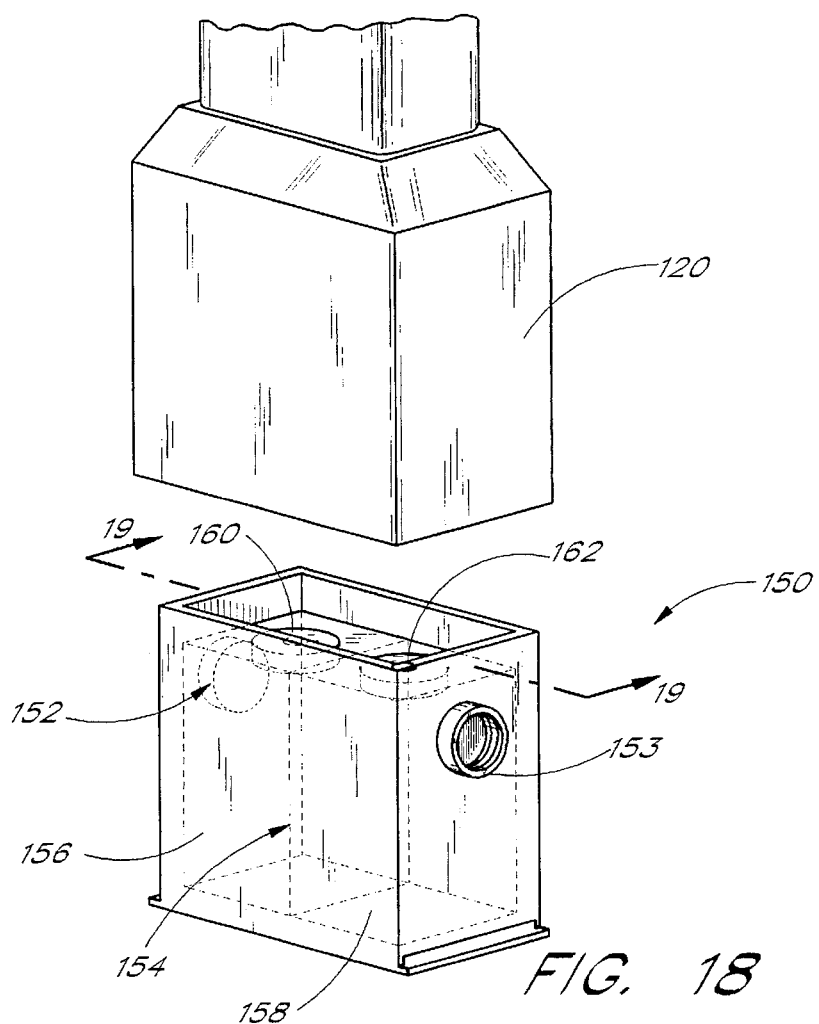
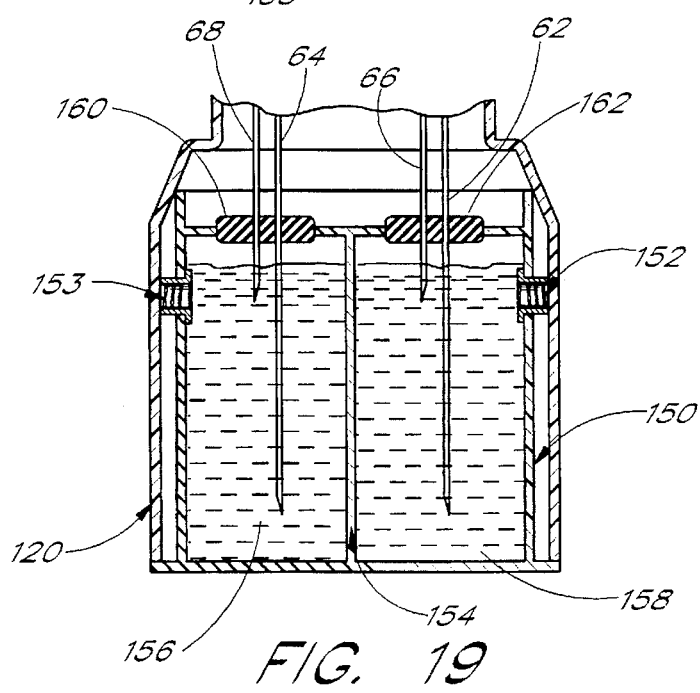

REFILLABLE FIBRINOGEN DISPENSING KIT

BACKGROUND OF THE INVENTION

The in vivo mechanism for the clotting of blood requires conversion of the soluble protein fibrinogen into the insoluble protein fibrin in a reaction catalyzed by the enzyme thrombin. Thrombin is the activated form of prothrombin, a globulin circulating in the plasma. The conversion of prothrombin to thrombin requires a number of reactions involving the interaction of blood fractions having thromboplastic activity, including Stewart-Prower factor, Factor V, Factor VIII, and calcium. Several additional substances having thromboplastic activity have been identified and are generally referred to by the genus thromboplastin.

Under the influence of thrombin, which is actually a proteolytic enzyme, and other blood factors, the blood protein fibrinogen loses several polypeptide chains to form fibrin. The fibrin then undergoes a polymerization to produce fibrin polymers which contribute to the physical properties of the clot.

The thrombin catalyzed polymerization of fibrinogen into fibrin is reproducible in vitro. For example, a system composed of purified fibrinogen, thrombin, and added calcium produces the so-called Fibrin S polymer by spontaneous reversible polymerization. Polymerization is said to be reversible due to the solubility of the Fibrin S polymer in dilute (0.03%) HCl.

However, an acid insoluble polymer of Fibrin I (insoluble fibrin) can be formed in vitro, for example, by addition of small amounts of serum to the in vitro system. The serum contains a factor responsible for inhibition of the reversible polymerization of fibrin. This stabilizing factor in serum which enters the clotting sequence after fibrin has been formed, known as the Laki-Lorand factor (LLF) or fibrin stabilizing factor (FSF), is known to exhibit a useful stabilizing effect on the in vitro polymerization of fibrinogen. Under the nomenclature proposed by the International Committee for the Standardization of the Nomenclature of Blood Clotting Factors, LLF is designated Factor XIII.

Thus, it is known that purified thrombin and fibrinogen, together with a variety of known adjuvants, can be combined in vitro to produce a polymer having great potential benefit, both as a hemostatic agent and as a tissue adhesive. Because of the rapid polymerization upon intimate interaction of fibrinogen and thrombin, it is important to maintain these two blood proteins separate until the application site. Previously, these materials have been delivered by devices such as a dual syringe apparatus which makes it possible to deliver the fluids for mixture at a small point.

One apparatus for applying a fibrinogen-based tissue adhesive is disclosed in U.S. Pat. No. 4,359,049 to Redl, et al. Redl discloses a complicated mechanism in which two standardized one-way syringes are held in a support having a common actuating means guided along a rod. Each of the delivery ends of the syringe is inserted into a collection manifold for delivery of the two components for mixing and delivery optimally through a mixing needle. However, it is often desirable or necessary to cover a broad area of a wound, either to stop bleeding, to fix tissue, or to prevent infection.

Notwithstanding the contribution of Redl, there remains a need for a fibrinogen dispensing kit which is inexpensive, suitable for entry into the sterile field, and adaptable for convenient recharging of the fibrinogen or thrombin from a single source, as may be required during prolonged surgery or other procedure. In addition, there is a need for a dispensing kit that is advantageously capable of delivering the two blood proteins either at a focused point of delivery or as an aerosol mist for covering a region of tissue.

SUMMARY OF THE INVENTION

There has been provided in accordance with one aspect of the present invention a dispenser for separately dispensing each of two biological fluids contained therein for intermixing at a remote site to produce hemostasis or a tissue adhesive, depending upon the application. The dispenser comprises a housing, having a first and a second pump therein. A first hollow aspirating tube in the housing is in fluid communication with the first pump, and a second hollow aspirating tube is in fluid communication with the second pump. A first and second reservoir for biological fluids are integrally formed in the housing. Each reservoir is provided with an injection port which is adapted to permit independent and sterile refilling of the reservoir. The first and second tubes extend within the housing into the first and second reservoirs, respectively. In a preferred embodiment, the first and second injection ports comprise a luer fitting with a resealable septum or self closing diaphragm.

In accordance with another aspect of the present invention, there is provided a dispenser, with a refillable cassette, for separately dispensing biological fluids contained therein for intermixing at a site outside of the dispenser. The dispenser of this embodiment features a housing having a chamber adapted to removably receive a cassette. The cassette has a first and second reservoir for biological fluids integrally formed within the cassette. A first and second fluid injection port is located on the first and second reservoir, respectively, to permit independent and sterile refilling of the reservoirs when the cassette is removed from the housing. A first and second hollow aspirating needle, in fluid communication with a first and second pump, respectively, is positioned in the housing so that when a loaded cassette is positioned in the chamber the first and second hollow aspirating needles provide a path of fluid communication between the cassette reservoirs and the pumps. When the pumps are activated, a flow of fluid is produced from the first and second reservoirs and out to the dispenser.

In accordance with another aspect of the present invention, there is provided a method for the sterile refilling of a biological fluid dispenser adapted for remote site intermixing of the fluids maintained separately therein. The method comprises providing a biological fluid dispenser with a separate first and second fluid reservoir, where each reservoir has a separate injection port. An external biological fluid source is then attached in a sterile manner to at least one of the injection ports. Biological fluid is then transferred from this external fluid source, through the injection port, and into the reservoir. The external biological fluid source is then disengaged from the injection port.

These and other features and advantages of the present invention will become apparent from the detailed description of preferred embodiments which follows, when taken together with the attached drawings and claims.

BRIEF DESCRIPTION OF THE DRAWINGS

FIG. 1 is an elevational perspective view of a dispenser.

FIG. 2 is a perspective view of the embodiment illustrated in FIG. 1, showing the cover open and exposing the container receiving areas.

FIG. 3 is a partial sectional front elevational view of an alternate dispenser.

FIG. 4 is a perspective view of the embodiment illustrated in FIG. 3.

FIG. 5 is a perspective view of an interface for loading the containers used, for example, in the dispenser FIGS. 1 and 2.

FIG. 6 is a perspective view of a dual fluid radial dispenser for dispensing fluid on the interior of a tubular vascular graft.

FIG. 7 is a perspective view of a single element from the radial dispenser shown in FIG. 6.

FIG. 8 is a partial cross-sectional view of the dispenser shown in FIG. 6.

FIG. 9 is a radial dispenser for dispensing fluids on the exterior surface of a tubular sleeve.

FIG. 10 is a perspective view of a single fluid dispensing element from the dispenser shown in FIG. 9.

FIG. 11 illustrates a spray pattern of a dispensing head, wherein intermixing occurs at a first distance from the spray head.

FIG. 12 is a dispenser head wherein intermixing occurs at a second distance from the spray head.

FIG. 13 illustrates a third embodiment of the spray head, wherein intermixing occurs at a focused point.

FIG. 14 illustrates a rigid attachment for conducting blood proteins to a remote location.

FIG. 15 illustrates an elongate flexible attachment for conducting blood proteins from the spray head to a remote location.

FIG. 16 is an exploded partial elevational perspective view of a dispenser in accordance with the removable cassette embodiment.

FIG. 17 is a partial sectional view of the cassette of FIG. 16, shown inserted into the dispenser.

FIG. 18 is an exploded partial elevational perspective view of a dispenser of the present invention featuring a removable and refillable cassette.

FIG. 19 is a partial sectional view of the cassette of FIG. 18, along lines 19—19, after the cassette has been inserted into the dispenser.

DETAILED DESCRIPTION OF PREFERRED EMBODIMENTS

Figure 4A:
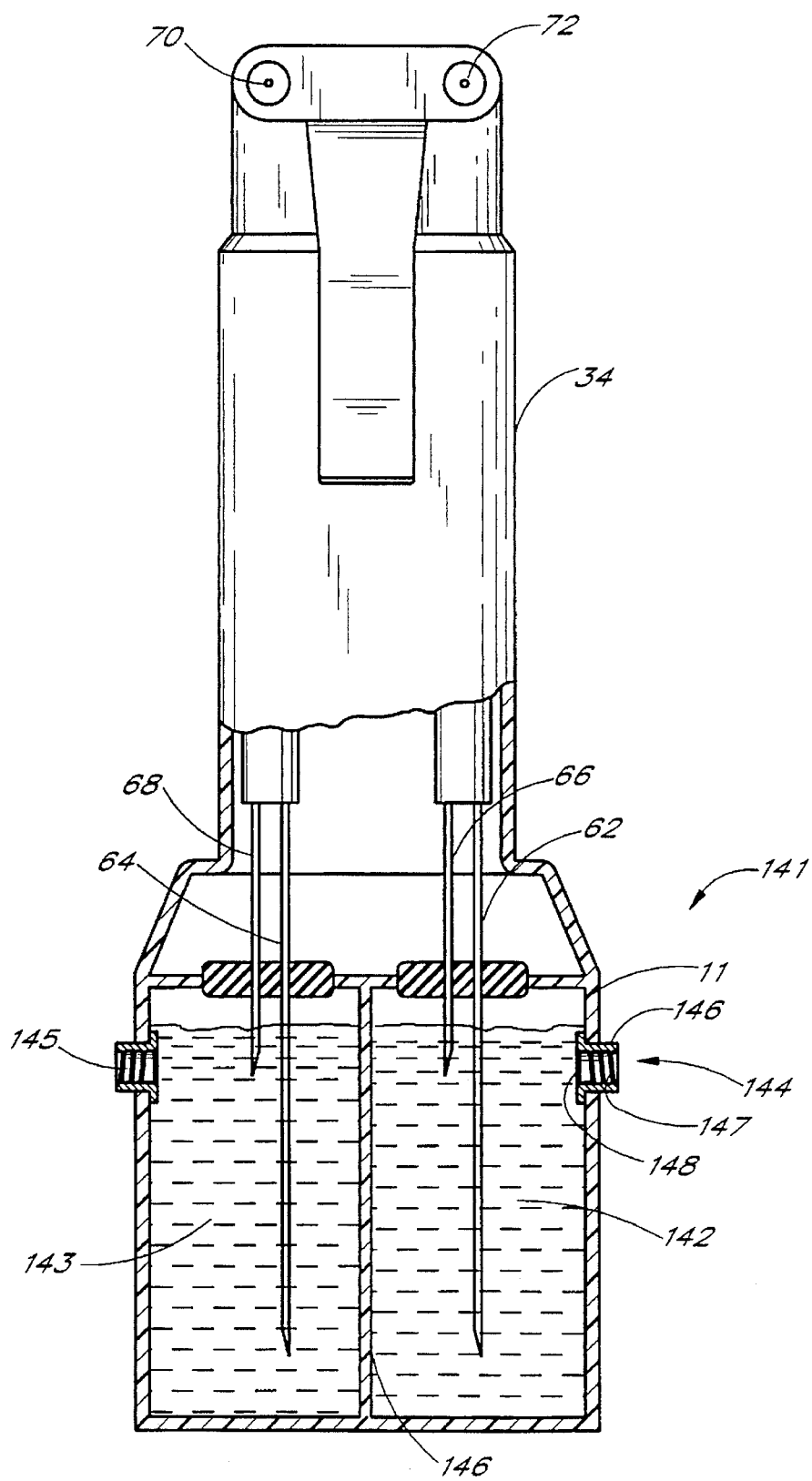
FIG. 4a is a partial sectional front elevational view of an embodiment of the invention adapted for refilling.

Referring to FIG. 1, there is illustrated a dispensing kit 10 according to one embodiment of the present invention. The dispenser 10 comprises a main housing 11 for enclosing the reservoirs of blood proteins and working parts of the dispenser. Housing 11 may be formed from any of a variety of materials and by any of a variety of processes as will be appreciated by one of skill in the art. Preferably, housing 11 is produced in two halves in accordance with known thermoplastic forming techniques, and optimally comprises acrylic, styrene, or other rigid thermoplastic material that is susceptible to sterilization and will remain substantially inert in the environment of the blood proteins to be dispensed.

Housing 11 comprises a container region 12 having a plurality of container receiving areas 14, 16 (illustrated in FIG. 2) adapted for removably receiving a plurality of containers 18, 20 (FIG. 3) for containing the fibrinogen and thrombin blood proteins. Optimally, a thermal insulation material 22 such as styrofoam or other conveniently formable insulating material is provided to surround the container receiving areas 14, 16 to maintain the blood proteins at an appropriate preselected temperature as will be discussed.

The container receiving areas 14, 16 are optimally further provided with a cover 24 for preventing accidental removal of the containers 18, 20. Cover 24 is provided with a hinge 26 and a latch 28 for engaging stop 30 on the housing for preventing accidental removal of the cover 24. Other convenient hinge and latch arrangements can be readily envisioned by one of skill in the art. Providing the housing 11 with a hinged cover 24 having a reversible latch 28 facilitates removal of empty containers 18, 20 and replacement with filled containers (not illustrated).

Referring to FIG. 4, the container region 12 of the dispensing kit 10 may further be provided with a window 32 for visual observation of the amounts of blood proteins remaining in the containers 18, 20.

Adjacent the container region 12 of the dispensing kit 10 is a pump region 34 which houses the pumping means for extracting a quantity of blood protein from each of the containers 18, 20 and delivering them to the application site. Thus, within the pump region 34 are contained a first pump 44 and a second pump 46. Pumps 44, 46 may be any of a variety of commercially available pumps, including, for example, a linear piston-type pump, as illustrated in the embodiment shown in FIG. 1, or a trigger sprayer-type pump, as illustrated in the embodiment of FIG. 3.

The particular pumping mechanisms to be utilized in the present invention is not critical, provided they may be conveniently ganged to a common actuator, and are susceptible to sterilization for entry into a sterile field. One example of a suitable trigger type sprayer is the Model TS-800 Trigger Sprayer from Calmar, Inc. of Watchung, N.J., which may conveniently be adjusted from a focused stream to a spray.

In the event that linear piston-type pumps, as illustrated in FIG. 1, are utilized, an actuator head 42 is additionally provided to form a unitary spray head 36 so that both the first and second pumps may be simultaneously operated. Actuator 42 can be molded from any of the same rigid thermoplastic materials used to mold the housing 11. Effluent ducts 70 and 72 are preferably adjustable so that each of the spray patterns illustrated in FIGS. 11–13 may be achieved. The ability to adjust the droplet size and the cross sectional area of interaction between the two effluent streams provides important flexibility to the clinician. The speed of formation of the fibrin polymer, and perhaps its strength are enhanced by a spray which permits intimate intermingling of droplets of the two fluids close to or at the application site.

Optimally, actuator 42 is removably linked to each of pumps 44 and 46 so that the pumps may be individually operated at the option of the clinician. In applications where hemostasis is sought, an actuator 42 or its functional equivalent will likely be preferred. However, it may be desirable in some circumstances to individually dispense the fluids, such as one on each opposing surface of the incision. This will delay the rapid polymerization until the two surfaces are brought into contact.

In accordance with another preferred embodiment of the present invention, illustrated in FIG. 4a, there is provided a dispensing kit 141 adapted for sterile and independent refilling of the fibrinogen and thrombin reservoirs. In this embodiment, the housing 11 is integrally formed to provide two reservoirs 142, 143, which are separated from one another by a retaining wall 146.

Reservoirs 142 and 143 are provided with injection ports 144 and 145, respectively, to allow independent refilling of each reservoir. Preferably, injection ports 144 and 145 are standard luer type connectors with self-closing diaphragms or resealable septums, to maintain the sterile field during the refilling operation. It can be appreciated, however, that other types of injection ports known by those of skill in the art to be suitable to maintain sterility during refilling may also be used.

For example, the illustrated injection port 144 comprises a generally cylindrically side wall 146 having a central, axially extending aperture therethrough. The interior surface of side wall 146 is provided with a standard thread 147, such as for rotationally receiving a male luer component. A distal end of the central aperture is sealed by an elastomeric material of any of a variety of types well known in the pierceable septum art.

The side wall 146 or other aperture defining structure can be integrally molded along with the wall of the container, as will be understood by those of skill in the art. Alternatively, an opening can be formed in the wall of a reservoir, such as during the molding process or in a post forming step such as by stamping or drilling operations. The separately formed injection port can then be secured within the opening by any of a variety of conventional techniques, such as threaded engagement, thermal or solvent bonding, adhesives, and the like.

In one embodiment, the septum 148 is secured to the injection port 144 throughout its annular circumference. In this embodiment, the filling instrument is preferably provided with a sharpened cannula such as a hypodermic needle for piercing the septum as is known in the art. Alternatively, the septum 148 is secured to the injection port 144 for less than its entire circumference, such as only throughout about 180 degrees or less of its circumference. In this manner, the septum can function as a check valve, thereby permitting fluid to enter the chamber 142 by forcing the unsecured end of the septum 148 away from its normal seat against the injection port 144, yet resist retrograde escape of the material therethrough.

Thus, in the embodiment of an injection port illustrated in FIG. 4a, introduction of media into the chamber 142 can be accomplished by piercing the septum 148 such as with a needle, or pushing the septum 148 away from its seat such as through fluid pressure, or using the blunt distal nose on a syringe or other loading device. In an embodiment intended to be refilled through the use of a needle, the pierceable septum 148 may be secured to the side wall of the container 142 in any of a variety of ways, and the tubular side wall 146 and thread 147 may not be necessary. Similarly, in a check valve embodiment in which septum 148 is intended to be displaced by the distal nose on a syringe, the internal thread 147 may not be necessary.

The orientation of the male and female components of the luer connector can be readily reversed as desired, as will be understood in the art. For example, the embodiment illustrated in FIG. 4a is provided with an internal thread on the interior of a female luer component, adapted to reversibly couple to a male luer component in fluid communication with a fluid source. Alternatively, the injection port 144 may be provided with a tubular element having an external thread or tabs on a proximal end thereof, spaced apart from the pierceable septum. In this manner, the injection port 144 would cooperate with many conventional syringes, which are often provided with a female connector component having a thread on the internal wall thereof. Optimizing the structure of the injection port 144 and 145 can be readily accomplished by one of ordinary skill in the art to suit the intended use environment, in view of the disclosure contained herein.

By providing the injection ports, the embodiment illustrated in FIG. 4a permits efficient and sterile refilling of either thrombin or fibrinogen, or both, as the need arises. Fibrinogen or thrombin can be drawn up in a syringe from a sterile external biological fluid source, and the filled syringe may then be attached to the appropriate injection port. The solution in the syringe may then be injected to fill the appropriate reservoir. Advantageously, vent needles 66 and 68, or other venting means known by those skilled in the art, are provided to minimize pressure build up within the reservoirs upon refilling.

Referring to FIG. 5, there is provided an interface device 50 adapted for placing a standard blood bag 52 or other container provided with a pierceable septum 56 in fluid communication with a container 18 suitable for use in embodiments of the dispensing kit 10 such as that illustrated in FIGS. 1–3. The interface 50 is provided at one end with a cannula 54 adapted for piercing the septum 56 contained on a standard blood bag 52. The interface 50 is further provided with a valve 58 which may be a stopcock, a pinch valve or any of a variety of known valving mechanisms for controlling the flow from the blood bag 52 into the container 18. The interface 50 is further provided with a hollow needle 60 in fluid communication by way of valve 58 with cannula 54, and adapted for piercing the resealable septum of a standard Vacutainer® or other vacuum bottle.

Evacuated sterile container 18 is typically provided with a pierceable septum 19 for maintaining a vacuum therein. In use, the interface 50 will be placed in fluid by way of cannula 54. With valve 58 in the closed position, the needle 60 on interface 50 is inserted through resealable septum 19 on container 18. When valve 58 is open, fluid contents from blood bag 52 are drawn into the interior of container 18 due top the vacuum contained therein. When sufficient contents have been transferred into the container 18, valve 58 is closed and container 18 is removed from needle 60. Container 18 is then ready for insertion into one of the container receiving areas 14, 16 on dispensing kit 10.

As container 18 is inserted into one of container receiving areas 14 or 16, the resealable septum 19 is first pierced by one of aspirating needles 62, 64. Aspirating needles 62, 64 are in fluid communication by way of pumps 44, 46 with effluent ducts 70, 72 on spray head 36. Aspirating needles 62, 64 are disposed such that when containers 18, 20 are fully inserted into the container receiving areas 14, 16, the needles will reach substantially to the bottom of the interior of the containers.

As the container 18 is further inserted into the container receiving area 14, resealable septum 19 will be pierced by a second vent needle 66. A vent needle 66, 68 is desirable to equalize pressure inside containers 18, 20, as fluid contents are drawn out through needle 62 or 64.

As an alternative to Vacutainer® containers 18 and 20, nonvacuum bottles could also be used in the dispensing kit 10 of the present invention. Sample bottles can be used which have a threaded neck such as to receive a cap, or which are provided with a luer or other mechanical interfit connection. The innermost extent of container receiving areas 14, 16 would be provided with a corresponding structure for engaging the luer or other interfit structure on the sample bottle. In this embodiment, it would be unnecessary for the aspirating needles 62, 64 to have sharpened ends.

In accordance with a further embodiment of the present invention, there is provided a modified dispensing kit adapted to receive the containers of fibrinogen and thrombin within a removable cassette. Referring to FIG. 16, there is illustrated in exploded form a dispenser 118 and cassette 122. As illustrated therein, housing 120 of dispenser 118 is adapted to slidably receive the upper end 126 of cassette 122. Cassette 122 may be produced in accordance with any of a variety of known methods, such as thermoplastic forming techniques, and optimally comprises acrylic, styrene or other rigid thermoplastic material. Cassette 122 may conveniently be formed in the same manner and of the same materials as the dispenser 10 described previously. In addition, cassette 122 is provided with insulation 132 for surrounding containers 123 and 124 as has been discussed.

The lower end 128 of cassette 122 is provided with a door 130 for providing access to the interior of the cassette 122. Door 130 is illustrated as a slidable panel, however, any of a variety of doors may be used as will be appreciated by one of skill in the art. Opening door 130 permits access to the interior of cassette 122 for insertion of containers 123 and 124, illustrated in phantom in FIG. 16. The upper end 126 of cassette 122 is provided with openings 125 and 127 to expose the containers 123 and 124 for providing fluid communication with the pumps, as will become apparent.

Cassette 122 is further provided with a pair of opposing surfaces 138 for providing friction so that the cassette may be conveniently gripped, such as between the thumb and forefinger, and inserted or withdrawn with respect to housing 120. Housing 120 is provided with a corresponding pair of openings 140 which expose the surfaces 138 when the cassette 122 is fully inserted into housing 120. Any of a variety of additional structures for facilitating removal of cassette 122 may be used, as will be apparent to one of skill in the art.

Referring to FIG. 17, there is disclosed a partial elevational cross-sectional view of a cassette embodiment of the dispenser of the present invention, illustrating the cassette 122 inserted into the housing 120. As seen therein, cassette 122 is dimensioned so that its exterior wall permits a snug fit with the interior of housing 120 for retaining the cassette therein. In addition, static friction will exist between each of needles 134 and 136, and the pierceable septums on containers 123 and 124, respectively, which are arranged in a similar manner as the needles and septums or other closures previously discussed. Any of a variety of structures well known to one of skill in the art may additionally be utilized for retaining cassette 122, such as releasably interlocking ridges and grooves on the interior surface of housing 120 and exterior surface of cassette 122 as will be appreciated by one of skill in the art.

As cassette 122 is inserted into housing 120, needles 134 and 136 pierce the corresponding closure members on containers 123 and 124, as has been previously discussed. For simplification purposes, vent needles, which have been discussed in connection with previous figures, have been deleted from FIG. 17.

The removable cassette embodiment accrues the important advantage in the operating room of providing a convenient bridge across the boundary of the sterile field. The dispensing kit 118, including the exterior of cassette 122 must be maintained sterile throughout a procedure in the operating room. However, the exterior of the containers themselves will not be sterile. The embodiment of FIGS. 16 and 17 enables the sterile nurse or physician to hold cassette 27 while the circulating nurse inserts filled containers 123 and 124 into cassette 122. The cassette 122 can then be fit onto housing 120 without compromising the integrity of the sterile field.

In another preferred embodiment, illustrated in FIGS. 18 and 19, cassette 122 is modified to permit independent and sterile refilling of biological fluids contained in the cassette. Referring now to FIG. 19, cassette 150 is integrally molded to provide two reservoirs 156 and 158, separated from one another by retaining wall 154. Cassette 150 is also provided with resealable septums 160 and 162, positioned over reservoirs 156 and 158, respectively, which are adapted to be pierced by the dispenser aspirating needles 62, 68. Reservoirs 156 and 158 are provided with injection ports 152 and 153, respectively, to permit independent refilling of each reservoir. Preferably, injection ports 152 and 153 are standard luer connectors with a self-closing diaphragm or resealable septum, as has been discussed, to maintain the sterile field during the refilling operation.

By providing the injection ports 152, 153, the reservoirs 156, 158, of cassette 150 may be independently and sterilely refilled with either thrombin or fibrinogen, or both, as the need arises. Once the fluids in cassette 150 are exhausted through use, cassette 150 may be withdrawn from housing 120 for refilling. Cassette 150 can then be quickly refilled by attaching a syringe filled with either thrombin or fibrinogen to the appropriate injection port on cassette 150. The solution in the syringe may then be injected into cassette 150 to fill the reservoir, and cassette 150 is then ready to be reinserted into dispenser housing 11. For particularly long surgical procedures, two cassettes may be desirable so that one can be refilled while the other is in use.

Preferably, cassette 150 is provided with means to vent pressure in or out which will occur within the reservoir upon filling and discharge. The particular venting mechanism used is not critical, provided that it is designed to maintain the sterility of the reservoirs during venting. For example, one such venting mechanism might include modifying septums 160 and 162 to include small shielded butterfly valves (not shown), which are adapted to open slightly to release internal reservoir pressure without compromising the sterility of the reservoir. Alternately, venting might be achieved by use of a separate vent needle, or by placing a small aperture in resealable septums 160 and 162.

In operation, a nurse or other attendant will typically reconstitute lyophilized thrombin from bovine or other source by mixing with water or isotonic saline diluents in accordance with known techniques. Lyophilized thrombin may be commercially obtained, for example, from the Parke-Davis division of Warner-Lambert Co. (Morris Plains, N.J.) which markets bovine thrombin in 5, 10 and 20 ml vials under the name Thrombostate®.

The reconstituted thrombin is then warmed to and maintained at approximately 37° celsius in the container 18 or 20 for installation in the dispenser 10. The fibrinogen is warmed from its refrigerated storage temperature to approximately 37° celsius and loaded into a blood bag if not so stored, or other suitable storage apparatus to be suspended from an IV pole in a location convenient to the operating table or other procedure site.

An interface device 50 is provided for the fibrinogen bag, and a fibrinogen container 18 is then filled as previously described and inserted into the dispensing kit 10 along with a bottle of reconstituted thrombin. Fibrinogen is typically available on an autologous basis or from a single donor source of plasma, which will be fractionated by a blood bank to produce a fibrinogen concentrate. Although fibrinogen extracts from multiple sources are commercially available in some countries, they are not yet in the United States due to certain prescreening difficulties known to those of skill in the art.

In the course of the surgical procedure, if additional fibrinogen and thrombin are necessary, additional vacuum bottles or other container 18 can be conveniently loaded from blood bag 52 or reconstituted and inserted into the dispensing kit 10 as needed. Alternately, a syringe or other injection device can be loaded from these sources, and the filled syringe can then be used to fill or refill the dispenser via the injection ports 144, 145, 152, 153. The ability to refill the dispensing kit 10 from a single source of each of the fibrinogen and thrombin accrues important advantages, particularly under circumstances when single source or autologous fibrinogen is being used.

As previously discussed, the fibrin polymer formed from the interaction of fibrinogen and thrombin may be advantageously applied in a variety of clinical situations. In addition to use as a tissue adhesive either during surgery or as a temporary emergency measure, and to the use of the fibrin polymer as a hemostatic agent, another important application relates to the implantation of vascular prostheses. Synthetic tubular grafts available for use in vascular surgery have been surgically implanted in hundreds of thousands of individuals over the course of the last decade. One such graft is comprised of rapidly stretched highly crystalline polytetrafluoroethylene, and is currently marked by W. L. Gore & Associates, Inc.

One difficulty associated with the implantation of woven or stretched vascular prostheses is the occurrence of leakage when initially sutured into the vascular system. Leakage is an inherent result of the desirability of having a porous structure to permit interweaving of the tissue, and can particularly be a problem if the patient has been anticoagulated through the use of such agents as heparin or other anticoagulants utilized in the operating room. Hence, it is advantageous to be able to pretreat the porous vascular graft prior to implantation to prevent leakage therethrough during the period of time required for the tissue growth to render the implant fluid-tight.

Thus, there is additionally provided in accordance with the present invention a radial spray head 74 for uniformly dispensing each of two solutions containing fibrinogen and thrombin, respectively, onto the interior surface of a tubular sleeve 76, as illustrated in FIG. 6. The tubular sleeve 76, illustrated in a cutaway view, may be any of a variety of commercially available Vascular prostheses as previously discussed. The radial spray head 74 comprises a first spray element 82 and a second spray element 84 in fluid communication by way of a first influent passage 78 and a second influent passage 80, respectively, with a source of the fibrinogen and thrombin containing solutions. The radial spray head 74 may be conveniently connected by way of a delivery conduit 110, such as that illustrated in FIG. 15, to the dispensing kit 10 of the present invention.

The radial spray head 74 is comprised of two spray elements 82, 84, which may be conveniently produced such as by a molding process to be identical to one another in configuration. For example, in FIG. 7 there is illustrated a single spray element 82 which arbitrarily has been designated as the first spray element 82 corresponding to FIG. 6. In the spray element 82, the influent passage 78 is in fluid communication with a plurality of effluent ducts 86 directed radially outwardly around the periphery of the spray element 82. Although the spray element 82 is illustrated as being substantially cylindrical in configuration, that is merely a preferred configuration due to the likelihood that most tubular vascular grafts will be of substantially circular cross section. However, for particular applications, it may be desirable to have a radial spray head 74 having a noncylindrical configuration depending upon the particular application.

As illustrated in each of FIGS. 6–8, the spray elements 82 and 84 are each provided with a passageway 88 which performs no function in the distal spray element 84. In the proximal spray element 82, however, the passageway 88 permits stacking of the proximal and distal spray elements on top of one another by receiving the second influent passage 80 therethrough. This design is selected for manufacturing convenience and, of course, other configurations could readily be devised.

Referring to the partial cross-sectional view in FIG. 8, it is seen that each of the influent passageways is respectively in fluid communication with the corresponding spray element. In a relatively large embodiment of the spray head 74, which may be desirable, for example, in applications utilizing larger arterial grafts, there may exist an undesirable dead space within the interior chamber 83 of element 82 so that a substantial quantity of fluid must be introduced into the spray element 82 before that element will express fluid uniformly around its periphery. Thus, it may be desirable to reduce the interior volume of the chamber 83. This can be accomplished, for example, by molding the spray element 82 such that only a relatively small annular flow passageway remains around the periphery of the spray element 82, for providing fluid communication between influent passage 78 and each of the effluent ducts 80.

The size and spacing of the effluent ducts 86 illustrated in FIGS. 6–8 is for illustrative purposes only, and a wide variety of duct patterns and spacings cold be utilizing in accomplishing the objectives of the present invention. In alternate embodiment, spray element 82 could be comprised of a top and a bottom half which form therebetween a single annular effluent duct extending radially all the way around the periphery of the spray element 82. The efficacy of a single annular groove embodiment would be dependent upon manufacturing tolerances, and the use of a plurality of drilled or molded effluent ducts 86 may therefore be superior.

In use, the radial spray head 74 may be placed in fluid communication with the dispensing kit 10 or other source of fluids by way of a delivery conduit 110 such as that illustrated in FIG. 15. Prior to implantation of the vascular graft, the radial spray head 74 may then be positioned within the vascular graft and drawn therethrough as fluid is expressed from the dispensing kit 10. In this manner, uniform quantities of the fibrinogen and thrombin solutions will be dispersed along the interior surface of the tubular sleeve 76, thereby forming a fluid-impermeable layer thereon.

As an alternative to or in addition to the interior spray head 74, there has further been provided in accordance with the present invention a spray element 90 for uniformly dispensing a plurality of fluids along the exterior of a tubular sleeve 76 (see FIG. 9). The radial spray head 90 comprises a first spray element 96 in communication with a source of fluid by means of first influent passage 92, and a second spray element 98 in communication with a source of fluid by way of second influent passage 94. Influent passages 92, 94 may be similarly placed in fluid communication with a source of fluids such as dispensing kit 10 by way of a delivery conduit 110. The first and second spray elements 96, 98 may be identical in configuration, and a single spray element 96 is illustrated in FIG. 10. Referring to FIG. 10, the first influent passage 92 is in fluid communication by way of an annular chamber (not illustrated) in spray element 96 with a plurality of effluent ports 100 dispersed radially around the interior of the torus-shaped element 96. The cylindrical opening through spray head 96 has a diameter to facilitate insertion of tubular sleeve 76 therethrough. As with the spacing of the effluent ducts 86 on the spray head 74 illustrated in FIG. 6, the frequency and configuration of the effluent ports 100 can vary considerably, however, it is contemplated that about ten or more effluent ports per inch of arc length along the interior cylindrical surface 101 of spray element 96 will be used.

Each element 96, 98 of the spray head 90 is illustrated with the influent passage disposed at a perpendicular to the plane of the spray element. This configuration may conveniently be accomplished by displacing the axis of effluent passage 92 radially outwardly from the exterior diameter of spray element 96. In this manner, identical spray elements can be stacked one on top of another without interference from influent passageways.

Of course, the configuration can be modified in a variety of ways and still accrue the advantages of the present invention. For example, the axis of effluent passageway 92 could coincide with the annular chamber within spray element 96. In that embodiment, the spray element 96 would need to be provided with an opening conceptually equivalent to passageway 88, illustrated in FIGS. 6–8, to permit stacking of the spray heads 96, 98. Alternatively, it may be desirable for the influent passageways 92, 94 to extend radially outwardly from the spray elements 96, 98 such that they extend at a perpendicular from the tubular sleeve 76 when in use. In this embodiment, the influent passageways could be integral with a handle for convenient operation of the spray head.

Use of the interior spray head 74 and exterior spray head 90 is advantageously accomplished through the use of a delivery conduit 110, illustrated in FIG. 15. Delivery conduit 110 is a dual channel conduit comprised of a flexible, resilient material which is substantially inert in the presence of the fibrinogen and thrombin solutions to be conducted therethrough. Distal end 112 can be secured in fluid communication with a spray head, such as that illustrated in FIGS. 6 or 9, by friction fit with the influent passageways thereof. Alternatively, any of a variety of other known connection means can be employed.

Similarly, proximal end 114 of delivery conduit 110 is advantageously dimensions to enable a friction fit to provide fluid communication with ducts 70 and 72 on spray head 36. Alternatively, proximal end 114 and spray head 36 can be provided with positive interlocking structure such as a luer connection or other known lock.

The delivery conduit 110 can be provided in a variety of different lengths, depending upon the intended use. Typically, vascular grafts for human implantation may be anywhere form about 10 cm to as long as 30 cm in length, or longer, and conduits of that length or less are currently envisioned. In another application of the present invention, a flexible delivery conduit 110 is provided having sufficient length to extend through the working channel in any of a variety of instruments such as an endoscope, arthroscope, or gastroscope which permits visualization at a remote site. This structure permits visualization and release of the fibrinogen and thrombin solutions at a remote spot in any of a variety of body cavities where hemostasis or an adhesive may be desired, such as a treatment for ulcerations in the stomach or gastrointestinal tract, or as a postoperative measure following such procedures as a tonsillectomy, adenoidectomy or more remote surgery. In a further embodiment, delivery conduit 108 (FIG. 14) is typically shorter than conduit 110, and is rigid for precisely controlled delivery at a more accessible specific point.

Although this invention has been described in terms of certain preferred embodiments, other embodiments that are apparent to those of ordinary skill in the art are also within the scope of this invention. Accordingly, the scope of the invention is intended to be defined only by reference to the appended claims.

I claim:

1. A refillable dispenser for separately dispensing each of two biological fluids contained therein for intermixing at a remote site to produce hemostasis or a tissue adhesive, comprising:

a housing having a dispenser head thereon for separately dispensing each of two fluids;

a first and second pump in the housing;

a first hollow aspirating tube in the housing, in fluid communication with the first pump;

a second hollow aspirating tube in the housing, in fluid communication with the second pump;

a first and second reservoir for biological fluids integrally formed in the housing;

a first fluid injection port on the housing for providing fluid communication between the first reservoir and a first external fluid source and a second fluid injection port on the housing for providing fluid communication between the second reservoir and a second external fluid source, the first and second injection ports being adapted to permit independent and sterile refilling of the first and second reservoirs; and wherein the first aspirating tube extends into the first reservoir and the second aspirating tube extends into the second reservoir, so that activation of the first and second pump produces a flow of biological fluid from the first and second reservoirs through the first and second aspirating tubes and out of the dispenser head for intermixing at a remote site outside of the dispenser.

2. A dispenser as in claim 1, wherein each of the first and second injection ports comprises a luer fitting with a self-closing diaphragm or resealable septum.

3. A dispenser for separately dispensing each of two biological fluids contained therein for intermixing at a site outside of the dispenser to product hemostasis or a tissue adhesive, said dispenser adapted for removably receiving a refillable cassette containing the biological fluids so that the dispenser may be refilled by removing an exhausted cassette, refilling the cassette under sterile conditions, and then reinserting the cassette into the dispenser, the dispenser comprising:

a dispenser housing having a chamber adapted for removably receiving a cassette;

a cassette removably disposed in the housing, the cassette having a first and a second reservoir for biological fluids integrally formed in the cassette, the cassette further having a first fluid injection port on the cassette for providing fluid communication between the first reservoir and a first external fluid source, and a second fluid injection port on the cassette for providing fluid communication between the second reservoir and a second external fluid source, the first and second injection ports being adapted to permit independent and sterile refilling of the first and second reservoirs after the cassette is removed from the housing;

a first and a second pump in the housing;

a first hollow aspirating needle in the housing, in fluid communication with the first pump and extending into the chamber so that when a loaded cassette is positioned in the chamber the first hollow needle will provide a path of fluid communication between the first reservoir and the first pump; and a second hollow aspirating needle in the housing, in fluid communication with the second pump and extending into the chamber so that when a loaded cassette is positioned in the chamber the second hollow needle will provide a path of fluid communication between the second reservoir and the second pump;

wherein the first and second pumps are placed in fluid communication with the first and second reservoirs, respectively, when the cassette is engaged with the dispenser housing, so that the first and second pump when activated, produce a flow of biological fluid from the first and second reservoirs through the first and second aspirating needles and out to the dispenser.

4. A refillable dispenser for separately dispensing each of two biological fluids contained therein for intermixing at a remote site to produce hemostasis or a tissue adhesive, comprising:

a housing having a dispenser head thereon for separately dispensing each of two fluids;

a first and second pump in the housing;

a first hollow aspirating tube in the housing, in fluid communication with the first pump;

a second hollow aspirating tube in the housing, in fluid communication with the second pump;

a first reservoir and a second reservoir for biological fluids positioned in the housing;

a first reservoir pump pathway positioned in the housing, and a first reservoir refill pathway positioned in the housing for providing fluid communication between the first reservoir and an external fluid source, and a second reservoir pump pathway positioned in the housing, and a second reservoir refill pathway positioned on the housing for providing fluid communication between the second reservoir and an external fluid source, wherein the first reservoir pump pathway is adapted to receive the first hollow aspirating tube, and the second reservoir pump pathway is adapted to receive the second hollow aspirating tube, and the first refill pathway is adapted to permit sterile and independent refilling of the first reservoir, and the second reservoir refill pathway is adapted to permit sterile and independent refilling of the second reservoir; and wherein the first hollow aspirating tube extends through the first reservoir pump pathway and into the first reservoir and the second hollow aspirating tube extends through the second reservoir pump pathway and into the second reservoir, so that activation of the first and second pump produces a flow of biological fluid from the first and second reservoirs through the first and second aspirating tubes and out of the dispenser head for intermixing at a remote site outside of the dispenser.

5. The dispenser of claim 4, wherein the first reservoir refill pathway and the second reservoir refill pathway further comprise a first and second luer fitting with a self-closing diaphragm or resealable septum.

6. A method for sterile refilling of a biological fluid dispenser adapted for remote site intermixing of fluids maintained separately therein, comprising the steps of:

providing a biological fluid dispenser with a separate first and second fluid reservoir, and a first and second fluid injection port on the first and second fluid reservoir, respectively, wherein the first and second fluid reservoirs are in fluid communication with a dispenser head which is adapted to spray biological fluids for intermixing at a remote site outside the biological fluid dispenser;

attaching an external biological fluid source in a sterile manner to at least one of the injection ports;

transferring biological fluid from the external biological fluid source through the injection port to at least one of the reservoirs without disrupting the fluid communication between the dispenser head and the reservoirs; and disengaging the external biological fluid source from the injection port.

7. The method of claim 6, wherein the injection ports are standard luer connectors and the external biological fluid source is a syringe filled with thrombin or fibrinogen.

* * * * *